(12) United States Patent
Van Benthem et al.

(10) Patent No.: US 6,660,869 B2
(45) Date of Patent: Dec. 9, 2003

(54) PREPARATION OF AN AROMATIC BISOXAZOLINE

(75) Inventors: Rudolfus A. T. M. Van Benthem, Limbricht (NL); Jacobus A. Loontjens, Meerssen (NL); Patrick H. M. Hendriks, Beek (NL); Bartholomeus J. M. Plum, Ulestraten (NL)

(73) Assignee: DSM N.V., Heerlen (NL)

( * ) Notice: Subject to any disclaimer, the term of this patent is extended or adjusted under 35 U.S.C. 154(b) by 27 days.

(21) Appl. No.: 10/041,666

(22) Filed: Jan. 10, 2002

(65) Prior Publication Data

US 2002/0091203 A1 Jul. 11, 2002

Related U.S. Application Data

(63) Continuation of application No. PCT/NL00/00446, filed on Jun. 27, 2000.

(30) Foreign Application Priority Data

Jul. 12, 1999 (NL) .............................................. 1012572

(51) Int. Cl.$^7$ .............................................. C07D 263/02
(52) U.S. Cl. ...................................................... 548/215
(58) Field of Search .......................................... 548/215

(56) References Cited

FOREIGN PATENT DOCUMENTS

| DE | 2155492 | 5/1973 |
|---|---|---|
| DE | 2319070 | 10/1974 |
| EP | 394849 | 10/1990 |

*Primary Examiner*—Joseph K. McKane
*Assistant Examiner*—Kamal Saeed
(74) *Attorney, Agent, or Firm*—Pillsbury Winthrop LLP

(57) ABSTRACT

The invention relates to a process for the preparation of an aromatic bisoxazoline in which, in a first step, an aromatic carboxylic acid or an ester hereof reacts with an alkanolamine, after which the hydroxyalkylamide obtained is in a second step converted into an aromatic bisoxazoline in the presence of a catalyst. The catalyst is phosphinic acid, a ($C_1$–$C_{26}$) alkyl phosphinic acid, a ($C_6$–$C_{20}$)aryl phosphinic acid or an ester or an anhydride derived from one of these acids.

9 Claims, No Drawings

PREPARATION OF AN AROMATIC BISOXAZOLINE

CROSS-REFERENCE TO RELATED APPLICATIONS

This is a Continuation of International Application No. PCT/NL00/00446 filed Jun. 27, 2000 which designated the U.S. and was published in the English language. The contents of this PCT application are incorporated in their entirety by reference.

BACKGROUND OF INVENTION (1) Field of Invention

The invention relates to a process for the preparation of an aromatic bisoxazoline such as for example phenylene-bis-oxazoline (PBO). The invention also relates to a powder paint binder composition and to a polymer composition comprising the aromatic bisoxazoline obtained with the process according to the present invention.

(2) Discussion of Prior Art

The preparation of an aromatic oxazoline such as for example 1,3-phenylene-bis-oxazoline is described in Liebigs Ann. Chem. (1974, 996–1009) by Witte and Seeliger. The product obtained with this process shows discolouration. Furthermore the process is relatively expensive because of the use of nitrites.

SUMMARY AND OBJECT OF INVENTION

It is the object of the present invention to provide a cheaper process for the preparation of an aromatic bisoxazoline such as for example PBO. The process has also to result in a product with the required properties.

The invention is characterised in that, in a first step, an aromatic carboxylic acid or an ester hereof reacts with an alkanolamine, after which the hydroxyalkylamide obtained is in a second step converted into an aromatic oxazoline in the presence of a catalyst.

The process according to the invention results in a relatively cheap product. This product is suitable to be used for example as a crosslinking agent in a powder paint binder composition or as a chain extender in polymer compositions.

DETAILED DESCRIPTION AND PREFERRED EMBODIMENTS

Suitable aromatic carboxylic acid or esters are for example di- or tricarboxylic acids or esters such as for example terephthalic acid, isophthalic acid, di($C_1$–$C_4$)alkyl terephthalate and/or di($C_1$–$C_4$)alkyl isophthalate.

Preferably dimethyl terephthalate and dimethyl isophthalate are applied.

Examples of suitable alkanolamines may be represented according to formula (I):

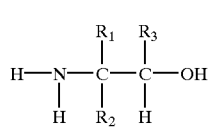

(I)

where $R^1$, $R^2$ and $R^3$ may be the same or different and may independently of one another be H, or a ($C_6$–$C_{10}$)aryl or ($C_1$–$C_8$)(cyclo)alkyl radical or $CH_2OH$.

Examples of suitable alkanolamines are ethanolamine, 1,1-dimethylethanolamine, isobutanolamine, β-cyclohexanolamine, isopropanolamine, 2-aminopropanol, 2-methyl-2-aminopropanol and/or trishydroxymethylmethylamine.

Preferably ethanolamine and/or isopropanolamine are applied.

Preferably the catalyst in the second step is an acid catalyst or a basic catalyst.

According to a preferred embodiment of the invention the catalyst is phosphinic acid, a ($C_1$–$C_{26}$) alkyl phosphinic acid, a ($C_6$–$C_{20}$) aryl phosphinic acid or an ester or an anhydride derived from any one of these acids or a catalyst with a cyclic structure such as 1,8-naphthalene diylphosphine ester acid (for example Struktol Polydis PD 3710™).

According to another preferred embodiment of the invention the catalyst is a compound according to formula (II) or formula (III):

(II)

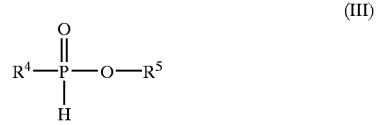

(III)

where
$R^4$=H, ($C_1$–$C_{26}$)alkyl or ($C_6$–$C_{20}$)aryl
$R^5$=H, ($C_1$–$C_{26}$)alkyl or ($C_6$–$C_{20}$)aryl and
$R^6$=H, ($C_1$–$C_{26}$)alkyl or ($C_6$–$C_{20}$)aryl.

According to a further preferred embodiment of the invention the catalyst is phenyl phosphinic acid.

The amount of catalyst in the second step will generally be between 0.05 and 3 wt. % (relative to the hydroxyalkylamide). Preferably this amount is between 0.5 and 2.2 wt. %.

Preferably there is no catalyst applied in the first step, however a catalyst may optionally also be added during the first step in an amount between for example 0.05 and 3 wt. %.

Suitable catalysts are, for example, metal salts of aliphatic carboxylic acids such as zinc acetate, magnesium stearate, lithium acetate, nucleophilic tertiary amines such as for example diaza[2,2,2]tricyclooctane (DABCO), diazabicycloundecene (DBU), dimethylaminopyridine (DMAP) and the catalysts mentioned for the second step.

Preferably, the catalyst used in the second step is the catalyst used in the first step.

The aromatic bisoxazoline obtained with the process according to the invention may be for example 1,3-PBO, 1,4-PBO, 1,2-naphthalene bisoxazoline, 1,8-naphthalene bisoxazoline, 1,1$^1$-dimethyl-1,3-PBO and 1,1$^1$-dimethyl-1,4-PBO.

According to another preferred embodiment of the invention the aromatic oxazoline is 1,4-PBO (2,2$^1$-(1,4-phenylene)bis-2,(4,5-dihydrooxazole).

Usually an excess amount of amine relative to the acid or ester is used in the first step. The molar ratio is usually between 1:2 and 1:4.

The reaction temperature in the first step will usually be between 20° C. and 200° C. and will be preferably between 70° C. and 180° C.

The temperature in the second step is usually between 100° C. and 250° C. and is preferably between 125° C. and 200° C.

This reaction may be carried out either with or without a solvent.

Preferably, the reaction in the second step is carried out in the presence of a solvent. Suitable solvents include for example xylene, propylene carbonate and/or acetic anhydride.

Preferably, the solvent is propylene carbonate.

On heating for example bis(2-hydroxyethyl) terephtphalamide a small amount of amine can be formed. Amines may deactivate some catalysts. Additives being capable to react with amines and that don't interfere with the desired reaction may optionally be used. Suitable additives include for example esters such as for example di- or tricarboxylic acids or esters such as for example terephthalic acid, isophthalic acid, di($C_1$–$C_4$)alkyl terephthalate and/or di($C_1$–$C_4$)alkyl isophthalate.

A product obtained with the process according to the invention may be used in many technical applications, such as for example as sizing agent, photosensitive material, solvent, cosmetic, membrane-separation material, emulsifier, surfactant, toner and monomer in polymer preparations.

The aromatic bisoxazoline obtained with the process according to the invention is particularly suitable for use as the crosslinking agent in a powderpaint composition or as a chain extender in a polyester or nylon composition.

Thermosetting powder paints have a better resistance to chemicals than thermoplastic powder paints. On account of this, attempts have for a long time been made to develop crosslinking agents and polymers for thermosetting powder coatings. Efforts are still being made to find binder compositions for thermosetting powder paints with good flow behaviour, good storage stability, low toxicity and good reactivity. A thermosetting binder composition for powder paints generally contains more than 50 wt. % polymer and less than 50 wt. % crosslinking agent.

The coating ultimately obtained with the powder paint must meet many, varying requirements. Various systems are known. Volatile components are released from some systems during curing. These systems present the disadvantage that they form coatings containing blisters and/or that undesired emissions are released. As far as the latter is concerned, the volatile component, if it is organic in origin, can cause undesired environmental or health problems. It has moreover been found that the desired properties of the powder paint or coating are not always all realised.

In many systems use is made of a polyester and a crosslinking agent that contains an epoxy group. In general, no volatile components are released from these systems. The use of bisphenol-A epoxy resins in so-called hybrid systems however results in coatings that show a relatively high degree of yellowing and chalking on exposure to UV light, while the commonly used cross-linking agent triglycidyl isocyanurate (TGIC) is toxicologically suspect.

It has been found that the use of the aromatic bisoxazoline, preferably PBO, as a cross-linking agent in binder compositions for powder paints results in a combination of highly desirable properties such as for example good flow behaviour and good resistance to chemicals, desired gloss without blistering of the surface up to and including layer thicknesses of at least 120 $\mu$m, a high resistance to scratching, good mechanical properties, good powder stability, good weather resistance and a good colour retention of the powder coating.

Depending on the desired final application, the aromatic bisoxazoline, preferably PBO, may also be used in combination with other crosslinking agents, such as for example triglycidyl isocyanurate (TGIC), polybisphenol-A-epoxides such as the various types of Epikote®, compounds containing (blocked) isocyanate groups, such as the caprolactam-blocked isophorone diisocyanate trimer, crosslinking agents containing β-hydroxyalkylamide groups such as Primid XL 522™ and polyfunctional oxazolines or a crosslinking agent that comprises at least one linear or branched aliphatic chain with 5–26 carbon atoms and has an epoxy functionality of more than 1, it being understood that the epoxy groups are carried by the at least one aliphatic chain such as for example epoxidised oil, with the oil being linseed oil, soybean oil, safflower oil, oiticica oil, caraway oil, rapeseed oil, castor oil, dehydrated castor oil, cottonseed oil, wood oil, vernonia oil (a natural oil), sunflower oil, peanut oil, olive oil, soy leaf oil, maize oil, fish oil such as herring or sardine oil and non-cyclic terpene oils.

It is also possible to apply a condensation polymer containing ester groups and at least one amide group in the backbone (as disclosed in WO 99/16810) as the second crosslinker.

The epoxidised oil is preferably epoxidised soybean oil and/or epoxidised linseed oil.

A binder composition for powder paints can contain the aromatic bisoxazoline, preferably PBO, as the crosslinking agent and a polymer containing carboxyl groups or anhydride groups as the polymer.

A polyester, a polyacrylate, a polyether (such as a polyether based on bisphenol or a phenol-aldehyde novolak), a polyurethane, a polycarbonate, a trifluoroethylene copolymer or a pentafluoropropylene copolymer, a polybutadiene, a polystyrene or a styrene-maleic anhydride copolymer can for example be chosen as the polymer.

Preferably the polymer is a polyester or a polyacrylate.

The polymer: crosslinking agent weight ratio is selected to depend on the desired final application and is generally between 95:5 and 80:20.

The preparation of thermosetting powder coatings in general and the chemical reactions for curing powder paints into cured coatings are described by Misev in Powder Coatings, Chemistry and Technology (1991, John Wiley), pp. 42–54, p. 148 and pp. 224–226. A thermosetting binder composition is generally defined as the resinous part of the powder paint consisting of polymer and crosslinking agent.

Common additives may optionally be used in the binder composition and in the powder paint system according to the invention, such as pigments, fillers, degassing agents, flow promoting agents and stabilisers. Suitable pigments are for example inorganic pigments, such as titanium dioxide, zinc sulphide, iron oxide and chromium oxide, and organic pigments such as azo compounds. Suitable fillers are for example metal oxides, silicates, carbonates and sulphates.

Primary and/or secondary antioxidants, UV stabilisers such as quinones, (sterically hindered) phenolic compounds, phosphonites, phosphites, thioethers and HALS compounds (hindered amine light stabilisers) can for example be used as stabilisers.

Examples of suitable degassing agents are benzoin and cyclohexanedimethanolbisbenzoate. Suitable flow-promoting agents are for example polyalkyl acrylates, fluorohydrocarbons and silicone oils. Other suitable additives are for example additives for improving the tribochargeability such as for example sterically hindered tertiary amines described in EP-B-371528.

Powder paints according to the invention may be applied in the usual manner, for example by electrostatically spraying the powder onto an earthed substrate and curing the coating by exposing it to heat at a suitable temperature for a sufficiently long period of time. The applied powder may for example be heated in a gas oven, an electrical oven or with the aid of infrared radiation.

Industrial applications of powder-paint (coating) compositions are described in a general sense in Powder Coatings, Chemistry and Technology, Misev, pp. 141–173 (1991).

Compositions according to the present invention may be used in powder coatings for use on for example metal, wood and plastic substrates. Examples are industrial coatings, coatings for machines and tools, household applications and parts of buildings. The coatings are also suitable for coating parts and accessories in the automotive industry.

According to a further preferred embodiment of the invention a polymer composition comprises a polymer, for example a polyester or a polyamide, and the aromatic bisoxazoline obtained with the specific process according to the present invention WO 96/34909 discloses a composition comprising a polyamide and a bisoxazoline. WO 96/34909 does not disclose or indicate the process according to the present invention.

As is evident from "The action of chain extenders" by Loontjens et al. (J. Appl. Pol. Sci 65, No. 9, 1997, 1813–1819), after polymerisation, polyesters and nylons have a molar mass that is often too low for industrial applications. The molar mass may be raised through a relatively expensive and laborious after-condensation. The molar weight may however also be raised by using the aromatic bisoxazoline according to the present invention, preferably PBO, as a chain extender.

The aromatic bisoxazoline according to the invention may also be used to improve the hydrolysis stability of a polyester.

The invention will be elucidated with reference to the following, non-limiting examples.

EXAMPLES

Experiment 1

Synthesis of bis-(β-hydroxyethyl)terephthalamide 194 grams of dimethylterephthalate were dissolved in 1 liter of xylene at 135° C. 128 grams of ethanolamine were added drop by drop. The methanol released was removed by means of distillation. After two hours' reaction bis-(β-hydroxyethyl)terephthalamide was isolated by means of filtration. The product was washed with xylene and was dried at 80° C. in a vacuum. The yield was 90%.

Example I

Synthesis of 1,4-phenylene-bisoxazoline 2.52 grams of bis-(β-hydroxyethyl)terephthalamide obtained according to Experiment 1 were dissolved in 20 ml of propylene carbonate. 2 wt. % phenylphosphinic acid was then added. The reaction mixture was stirred for 42 hours at 175° C. NMR (nuclear magnetic resonance) analysuis of the filtrate showed that the overall yield was 60%.

Example II

A powder paint composition comprising 200 parts by weight acid functional polyester (Uralac P2220 of DSM Resins), 30 parts by weight of the crosslinker obtained in Example I, 0,8 parts by weight of benzoin, 100 parts by weight titanium dioxide (Kronos 2160) and 3 parts by weight flow agent (Resiflow) were mixed in an extruder at 100° C. The extrudate was cooled, ground and sieved and the sieve fraction smaller than 90 micrometers was used as a powder coating. The powder paint was sprayed electrostatically onto an aluminium panel. The panel was cured in a furnace at 200° C. for 15 minutes. The reverse impact was 165ip (according to ASTM 2794/69).

What is claimed is:

1. A process for the preparation of an phenylene or napthalene bisoxazoline, wherein, in a first step, an phenylene or napthalene carboxylic acid or an ester thereof reacts with an alkanolamine, after which the hydroxyalkylamide obtained is in a second step converted into an phenylene or napthalene bisoxazoline in the presence of a catalyst.

2. A process according to claim 1, wherein the phenylene or napthalene carboxylic acid or the ester hereof is terephthalic acid, isophthalic acid, di($C_1$–$C_4$)alkyl terephthalate and/or di($C_1$–$C_4$)alkyl isophthalate.

3. A process according to claim 2, wherein the phenylene or napthalene carboxylic acid or the ester is dimethyl terephthalate or dimethyl isophthalate.

4. A process according to claim 1, wherein the alkanolamine is ethanolamine and/or isopropanolamine.

5. A process according to claim 1, wherein the catalyst is an acid catalyst or a basic catalyst.

6. A process according to claim 5, wherein the catalyst is phosphinic acid, a ($C_1$–$C_{26}$) alkyl phosphinic acid, a ($C_6$–$C_{20}$) aryl phosphinic acid or an ester or an anhydride derived from one of these acids.

7. A process according to claim 5, wherein the catalyst is a compound according to formula (II) or formula (III):

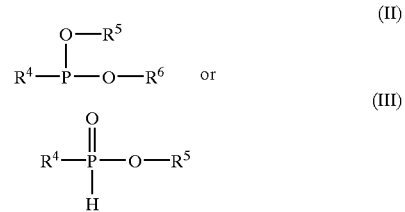

where
$R^4$=H, ($C_1$–$C_{26}$)alkyl or ($C_6$–$C_{20}$)aryl
$R^5$=H, ($C_1$–$C_{26}$)alkyl or ($C_6$–$C_{20}$)aryl and
$R^6$=H, ($C_1$–$C_{26}$)alkyl or ($C_6$–$C_{20}$)aryl.

8. A process according to claim 7, wherein the catalyst is phenyl phosphinic acid.

9. A process according to claim 1, wherein the second step is carried out in the presence of propylene carbonate.

* * * * *